(12) United States Patent
Baubeau et al.

(10) Patent No.: US 12,076,276 B2
(45) Date of Patent: Sep. 3, 2024

(54) CUTTING DEVICE WITH OPTICAL COUPLER INCLUDING A POLARISATION CORRECTOR

(71) Applicant: KERANOVA, Saint Etienne (FR)

(72) Inventors: Emmanuel Baubeau, Saint Etienne (FR); Sylvie Nadolny, Saint Etienne (FR)

(73) Assignee: KERANOVA, Saint Etienne (FR)

( * ) Notice: Subject to any disclaimer, the term of this patent is extended or adjusted under 35 U.S.C. 154(b) by 367 days.

(21) Appl. No.: 17/627,827

(22) PCT Filed: Jul. 17, 2020

(86) PCT No.: PCT/EP2020/070302
§ 371 (c)(1),
(2) Date: Jan. 18, 2022

(87) PCT Pub. No.: WO2021/013734
PCT Pub. Date: Jan. 28, 2021

(65) Prior Publication Data
US 2022/0257413 A1    Aug. 18, 2022

(30) Foreign Application Priority Data

Jul. 19, 2019   (FR) ..................... 1908208

(51) Int. Cl.
*A61F 9/008*   (2006.01)
*A61B 18/20*   (2006.01)
*A61B 18/22*   (2006.01)

(52) U.S. Cl.
CPC ............ *A61F 9/008* (2013.01); *A61B 18/201* (2013.01); *A61B 2018/2227* (2013.01); *A61F 2009/0087* (2013.01); *A61F 2009/00872* (2013.01)

(58) Field of Classification Search
CPC .............. A61F 9/008; A61F 2009/0087; A61F 2009/00872; A61F 2009/00897;
(Continued)

(56) References Cited

U.S. PATENT DOCUMENTS

2004/0147378 A1   7/2004 Conklin et al.
2017/0340483 A1   11/2017 Rill

FOREIGN PATENT DOCUMENTS

CN   103001106 A   3/2013
CN   103148795 A   4/2016
(Continued)

OTHER PUBLICATIONS

English translation of the First Office Action issued by the China National Intellectual Property Administration in connection with Chinese patent application No. 2023111301779390 on Nov. 13, 2023, 7 pages.
(Continued)

*Primary Examiner* — Scott M. Getzow
(74) *Attorney, Agent, or Firm* — BCF LLP

(57) ABSTRACT

The present invention relates to a cutting device comprising: a laser source (1) for emitting an initial laser beam (11) in the form of pulses, a shaping system (2) positioned downstream of the femtosecond laser (1), for transforming the initial laser beam (11) into a single phase-modulated laser beam, an optical coupler (3) between the laser source (1) and the shaping system (2), the optical coupler (3) including an optical fibre (31), remarkable in that the cutting device further comprises a polarisation corrector (7) for modifying the polarisation of the initial laser beam (11) at an input end of the optical coupler (3) such that the polarisation of the laser beam at an output end of the optical coupler (3) corresponds to a desired reference polarisation.

17 Claims, 3 Drawing Sheets

(58) Field of Classification Search
CPC ......... A61F 2009/00853; A61B 18/201; A61B 2018/2227
See application file for complete search history.

(56) References Cited

FOREIGN PATENT DOCUMENTS

| | | |
|---|---|---|
| EP | 0058708 A1 | 5/1985 |
| EP | 0145502 A2 | 6/1985 |
| EP | 3266403 A1 | 1/2018 |
| FR | 3026940 A1 | 4/2016 |
| FR | 3049847 A1 | 10/2017 |
| FR | 3049848 A1 | 10/2017 |
| RU | 2017116053 A | 11/2018 |
| WO | 2008/055506 A2 | 5/2008 |
| WO | 2012158183 A1 | 11/2012 |
| WO | 2016055539 A1 | 4/2016 |
| WO | 2016058931 A2 | 4/2016 |
| WO | 2017/182342 A1 | 10/2017 |
| WO | 2017174710 A1 | 10/2017 |
| WO | 2019001795 A1 | 1/2019 |
| WO | 2019/145484 A1 | 8/2019 |
| WO | 2019/145487 A1 | 8/2019 |

OTHER PUBLICATIONS

English translation of the Office Action issued by the Russian Patent Office in connection with Russian patent application No. 2022104275 on Oct. 17, 2023, 6 pages.

Russell, Philip, "Photonic Crystal Fibers", Science, vol. 299, Jan. 17, 2003.

CUTTING DEVICE WITH OPTICAL COUPLER INCLUDING A POLARISATION CORRECTOR

CROSS-REFERENCE TO RELATED APPLICATIONS

This application is a national phase filing under 35 U.S.C. § 371 of International Application No. PCT/EP2020/070302 filed on Jul. 17, 2020, which claims benefit of priority from French Patent Application No. 1908208 filed Jul. 19, 2019, the contents of which are hereby incorporated by reference in their entirety.

TECHNICAL FIELD

The present invention relates to the technical field of the treatment of eye diseases performed using a femtosecond laser, and more particularly the field of ophthalmological surgery in particular for corneas or lenses cutting applications.

The invention relates to a device for cutting human or animal tissue, such as a cornea, or a lens, by means of a femtosecond laser.

By femtosecond laser is meant a light source able to emit a laser beam in the form of ultra-short pulses, whose duration is comprised between 1 femtosecond and 100 picoseconds, preferably between 1 and 1,000 femtoseconds, in particular approximately a hundred femtoseconds.

PRIOR ART

It has already been proposed to perform eye surgeries by means of a femtosecond laser, such as operations for cutting corneas or lenses.

Document FR 3 026 940 describes a cutting apparatus including a laser source and a shaping system. Document US 2017/340483 describes a system for eye surgery comprising: a laser system, an operating microscope, a control unit, a frame, a first hinged arm on which a head of the operating microscope is attached and a second hinged arm on which an applicator head of the laser system is attached, the two heads being able to be connected to each other.

The international applications PCT/EP2019/051872 and PCT/EP2019/051876 dated Jan. 25, 2019 filed on behalf of the Applicant describe an apparatus for cutting human or animal tissue, such as a cornea or a lens.

Referring to FIG. 1, this apparatus includes:
- a femtosecond laser source 1 for emitting an initial laser beam in the form of pulses,
- a shaping system 2—such as a spatial light modulator (SLM)—positioned downstream of the laser source 1, for transforming the initial laser beam into a single phase-modulated laser beam, the shaping system being able to modulate the phase of the wavefront of the initial laser beam according to a modulation set value calculated to distribute the energy of the laser beam into at least two impact points forming a pattern in a focusing plane 81,
- an optical coupler 3 between the femtosecond laser source 1 and the shaping system 2, the optical coupler 3 including a photonic crystal optical fiber for filtering the laser beam 11 derived from the femtosecond laser source 1,
- an sweeping optical scanner 4, positioned downstream of the shaping system 2, for moving the pattern along a predefined movement path in the focusing plane 81,
- an optical focusing system 5, positioned downstream of the sweeping optical scanner 4, for moving the focusing plane 81 of the modulated laser beam in a cutting plane for the desired tissue 7,
- a control unit 6 for driving the shaping system 2, the optical coupler 3, the sweeping optical scanner 4 and the optical focusing system 5.

Advantageously, this cutting device can be integrated into a hinged arm. More specifically, the shaping system 2, the sweeping optical scanner 4 and the optical focusing system 5 can be mounted in a chamber (hereinafter referred to as "working head") attached to a free end of the hinged arm, while the laser source 1 and the control unit 6 can be integrated into a casing of the hinged arm, the optical coupler 3 extending between the casing and the working head to propagate the laser beam 11 between the laser source 1 and the shaping system 2.

The optical coupler 3 allows simplifying the cutting device by facilitating the transmission of the laser beam 11 between the laser source 1 and the shaping system 2 which are distant. Indeed, because of its significant bulk, the laser source 1 cannot be positioned in the working head of the hinged arm.

However, when traveling through the photonic crystal fiber, the laser beam 11 derived from the laser source 1 undergoes a variation in its polarization. This polarization variation depends on the position and orientation of the photonic crystal fiber (which depends on the position and orientation of the working head relative to the casing of the hinged arm).

However, since the shaping system 2 is sensitive to the polarization of the laser beam, this polarization variation induces a reduction in the power of the modulated laser beam at the output of the shaping system 2.

One aim of the present invention is to propose a technical solution for maintaining the full power of the modulated laser beam regardless of the position and orientation of the shaping system 2 relative to the laser source 1.

DISCLOSURE OF THE INVENTION

To this end, the invention proposes an apparatus for cutting human or animal tissue, such as a cornea, or a lens, said apparatus including:
- a laser source for emitting a treatment laser beam in the form of pulses,
- a shaping system—such as a spatial light modulator (SLM)—positioned downstream of the laser source, for transforming the treatment laser beam into a single phase-modulated treatment laser beam, the shaping system being able to modulate the phase of the wavefront of the treatment laser beam according to a modulation set value calculated to distribute the energy of the treatment laser beam into at least two impact points forming a pattern in a focusing plane,
- an optical coupler between the laser source and the shaping system, the optical coupler including a photonic crystal optical fiber, remarkable in that the cutting apparatus further comprises a polarization corrector for modifying the polarization of the treatment laser beam upstream of the shaping system, so that the polarization of the treatment laser beam at the input of the shaping system corresponds to a desired reference polarization, the polarization corrector being mounted upstream of the shaping system. Advantageously, the polarization corrector can comprise:

means for measuring a polarization variation between an input end of the optical coupler and an output end of the optical coupler, and means for modifying the polarization of the treatment laser beam upstream of the optical coupler so as to compensate for the measured polarization variation.

The presence of a polarization corrector allows modifying the polarization of the initial laser beam at the input of the optical coupler so that the polarization of the laser beam at the output of the optical coupler is substantially equal to a desired reference polarization for the laser beam before its introduction into the shaping system. This desired reference polarization corresponds to the polarization of the laser beam for obtaining maximum power for the modulated laser beam at the output of the shaping system.

In the context of the present invention, it is meant by "impact point" an area of the laser beam comprised in its focal plane in which the intensity of said laser beam is sufficient to generate a gas bubble in a tissue.

In the context of the present invention, it is meant by "adjacent impact points" two impact points disposed facing each other and not separated by another impact point. It is meant by "neighboring impact points" two points in a group of adjacent points between which the distance is minimal.

In the context of the present invention, it is meant by "pattern" a plurality of laser impact points generated simultaneously in a focusing plane of a shaped laser beam—that is to say phase-modulated for distributing its energy into several distinct spots in the focusing plane corresponding to the cutting plane of the device. Thus, the shaping system allows modifying the intensity profile of the laser beam in the cutting plane, so as to be able to improve the quality or the speed of the cut depending on the chosen profile. This modification of the intensity profile is obtained by modulation of the phase of the laser beam.

The optical phase modulation can be performed by means of a phase mask. The energy of the incident laser beam is conserved after modulation, and the shaping of the beam is performed by acting on its wavefront. The phase of an electromagnetic wave represents the instantaneous situation of the amplitude of an electromagnetic wave. The phase depends on both time and space. In the case of the spatial shaping of a laser beam, only the space variations of the phase are considered.

The wavefront is defined as the surface of the points of a beam having an equivalent phase (i.e. the surface made up of the points whose travel times from the source having emitted the beam are equal). Changing the spatial phase of a beam therefore involves changing its wavefront.

This technique allows carrying out the cutting operation in a faster and more efficient manner because it implements several laser spots, each performing a cut and according to a monitored profile.

Positioning the optical coupler including the photonic crystal optical fiber between the femtosecond laser and the shaping system allows avoiding any disturbance in the shaping of the laser beam performed by the shaping system.

Preferred but non-limiting aspects of the cutting apparatus are as follows:

the polarization corrector can be mounted between the laser source and the shaping system, said polarization corrector being able to modify the polarization of the treatment laser beam upstream of the optical coupler so that the polarization of the treatment laser beam downstream of the optical coupler corresponds to the desired reference polarization;

the measuring means can be optically connected to the output end of the optical coupler, said measuring means being able to measure a polarization variation of the treatment laser beam from a measurement laser beam generated by the laser source, the intensity of the measurement laser beam being lower than the intensity of the treatment laser beam;

the measuring means may comprise:
 a polarizer for selectively filtering a polarization plane of the measurement laser beam, and
 a polarization analyzer mounted downstream of the polarizer for measuring information representative of the polarization of the measurement laser beam at the output of the optical coupler;

the measuring means may further comprise a computer for calculating, from the information measured by the polarization analyzer, a polarization variation $\Delta_{polarization}$ between:
 the polarization of the measurement laser beam emitted by the laser source, and
 the polarization of the measurement laser beam received by the polarization analyzer;

the means for modifying the polarization of the treatment laser beam can be disposed between the laser source and the optical coupler, said means for modifying the polarization being able to pivot the polarization plane of the treatment laser beam upstream of the optical coupler by an angle opposite to the measured polarization variation;

the desired reference polarization can be equal to the polarization of the treatment laser beam at the output of the laser source (i.e. before traveling through the polarization corrector and the optical coupler);

the cutting apparatus may further comprise:
 an sweeping optical scanner, positioned downstream of the shaping system, for moving the pattern along a predefined movement path in the focusing plane,
 an optical focusing system, positioned downstream of the sweeping optical scanner, for moving the focusing plane of the modulated laser beam in a cutting plane for the desired tissue,
 a control unit for driving the laser source, the shaping system, the optical coupler, the sweeping optical scanner and the optical focusing system.

The invention also relates to a therapy device including a casing and a hinged arm mounted on the casing, the arm including several arm segments connected by hinges, remarkable in that the therapy device further comprises a cutting apparatus as described above, the shaping system, the sweeping optical scanner and the optical focusing system being mounted in an end segment of the hinged arm, the laser source and the control unit being integrated into the casing.

Advantageously, the means for modifying the polarization of the treatment laser beam can be integrated into the casing.

BRIEF DESCRIPTION OF THE DRAWINGS

Other characteristics and advantages of the invention will emerge clearly from the description which is given below, by way of indication and without limitation, with reference to the appended figures, in which.

DETAILED DISCLOSURE OF THE INVENTION

Figure 1:
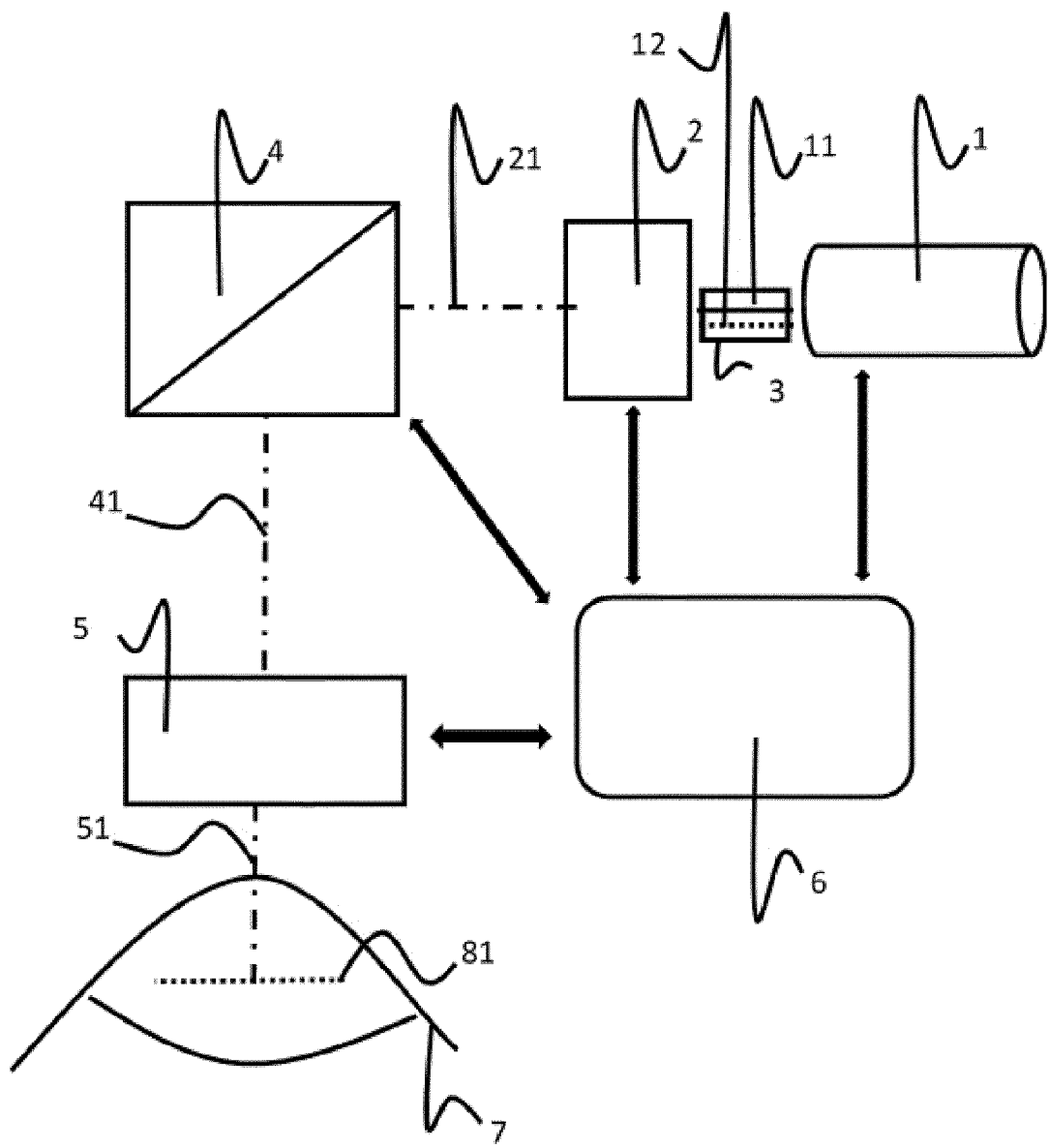
FIG. 1 is a schematic representation of a mounting including a cutting apparatus.

The invention relates to an apparatus for cutting human or animal tissue by means of a femtosecond laser source. In the remainder of the description, the invention will be described, by way of example, for the cutting of a cornea of a human or animal eye, it being understood that the present invention can be used for any other type of treatment of an ocular tissue.

1. OVERVIEWS

1.1. Cutting Apparatus

As indicated above, the cutting apparatus comprises:
- a femtosecond laser source 1 able to emit a treatment laser beam 11 in the form of high intensity pulses,
- a shaping system 2, positioned downstream of the laser source 1, for modulating the phase of the treatment laser beam 11 and obtaining a single modulated laser beam 21 in which the energy of the treatment laser beam 11 is distributed into a plurality of impact points in its focal plane, this plurality of impact points defining a pattern,
- an optical coupler 3 between the laser source 1 and the shaping system 2, the coupler allowing the propagation of the treatment laser beam 11 derived from the laser source 1 to the shaping system 2,
- an sweeping optical scanner 4 downstream of the shaping system 2, the sweeping optical scanner 4 for orienting the modulated laser beam 21 to move the pattern along a movement path predefined by the user in a focusing plane 81,
- an optical focusing system 5 downstream of the sweeping optical scanner 4, the optical focusing system for moving the focusing plane 81—corresponding to the cutting plane—of the deflected laser beam 41 derived from the sweeping optical scanner 4,
- a control unit 6 for driving the laser source 1, the shaping system 2, the optical coupler 3, the sweeping optical scanner 4 and the optical focusing system 5.

The shaping system 2 allows modulating the phase of the treatment laser beam 11 derived from the laser source 1 to form intensity peaks in the focusing plane 81, each intensity peak producing a respective impact point in the focal plane corresponding to the cutting plane. The shaping system 2 is, according to the illustrated embodiment, a liquid crystal Spatial Light Modulator, known as SLM. In a known manner, the SLM implements a phase mask, that is to say a map determining how the phase of the treatment laser beam must be modified in order to obtain a given amplitude distribution in its focusing plane 81. The use of such a shaping system allows on the one hand reducing the cutting time of the biological tissue (by generating several impact points simultaneously), and on the other hand obtaining substantially equal impact points (the shape, the position and the diameter of each point being dynamically monitored by a phase mask calculated and displayed on the shaping system).

The optical coupler 3 allows the transmission of the treatment laser beam 11 between the laser source 1 and the shaping system 2. The optical coupler 3 advantageously comprises an optical fiber. This optical fiber can be a Photonic-Crystal Fiber or PCF, and in particular a hollow-core photonic crystal fiber. A hollow-core photonic crystal fiber is particularly adapted to the propagation of short high-energy laser pulses. The use of such a fiber is therefore advantageous for optimally conveying the treatment laser beam 11 derived from the laser source 1.

1.2. Therapy Device

Figure 2:
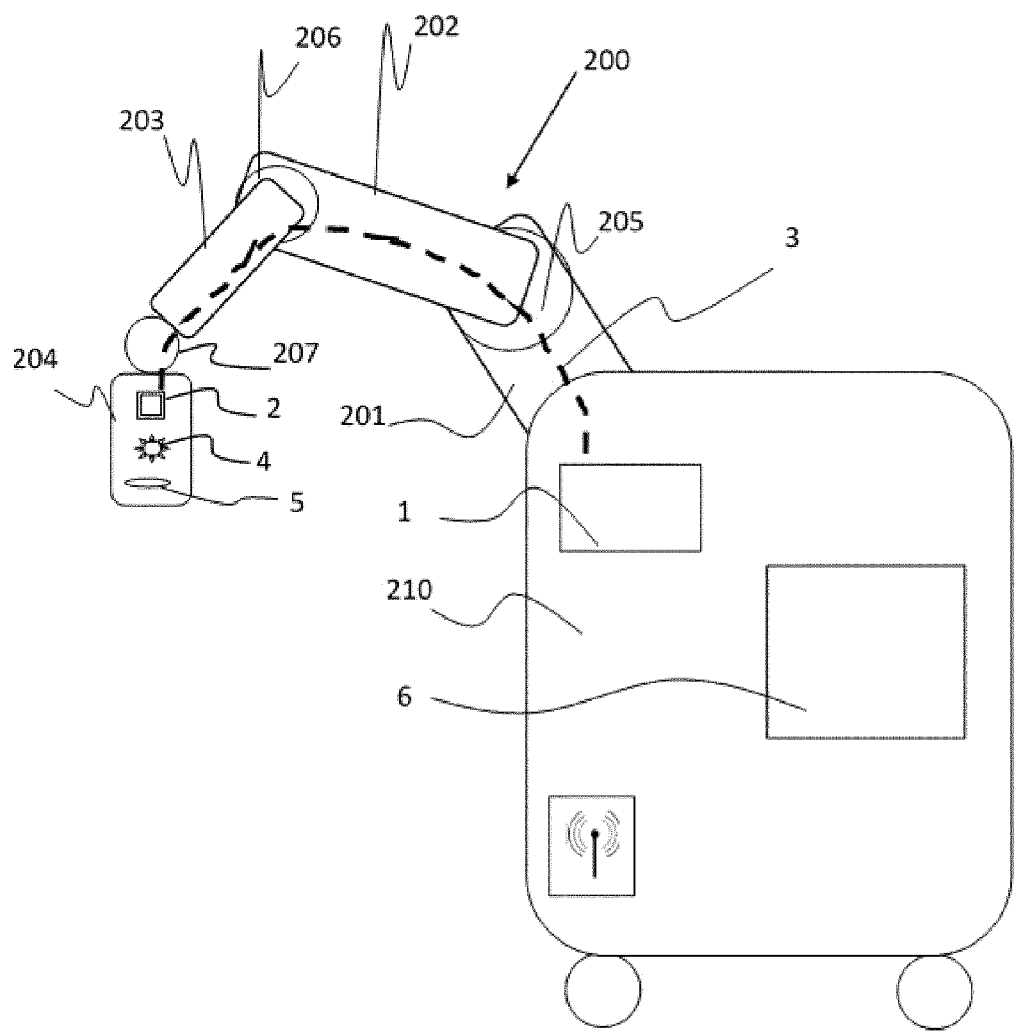
FIG. 2 is a schematic representation of a therapy device with a hinged robotic arm integrating the cutting apparatus illustrated in FIG. 1.

Thanks to the use of an optical coupler 3, the cutting apparatus can be mounted in a therapy device including a hinged arm 200 and a fixed casing 210 on which the hinged arm 200 is mounted, as illustrated in the FIG. 2. However, the reader will appreciate that the cutting apparatus is not necessarily mounted in a therapy device including an arm and a fixed casing. Particularly, the therapy device can be used alone, that is to say without being mounted in a hinged arm and a casing.

The arm 200 comprises several arm segments 201-204 connected by motorized hinges 205-207 (pivot or ball joints) to allow the automatic rotational movement of the various segments 201-204 relative to each other.

The arm 200 is able to move between:
- a rest position (not represented) facilitating its transport from one operating room to another and/or inside an operating room, and
- a working position in which the end of the arm 200 extends above the ocular tissue to be treated.

The shaping system 2, the sweeping optical scanner 4 and the optical focusing system 5 can be mounted in the end segment 204 (i.e. "working head") of the arm 200.

The laser source 1 and the control unit 6 can be integrated into the movable casing 210 of the therapy device, the optical coupler 3 extending between the casing 210 and the end segment 204 to propagate the treatment laser beam 11 derived from the laser source 1 to the shaping system 2.

2. POLARIZATION CORRECTOR

2.1. Overviews

Figure 3:
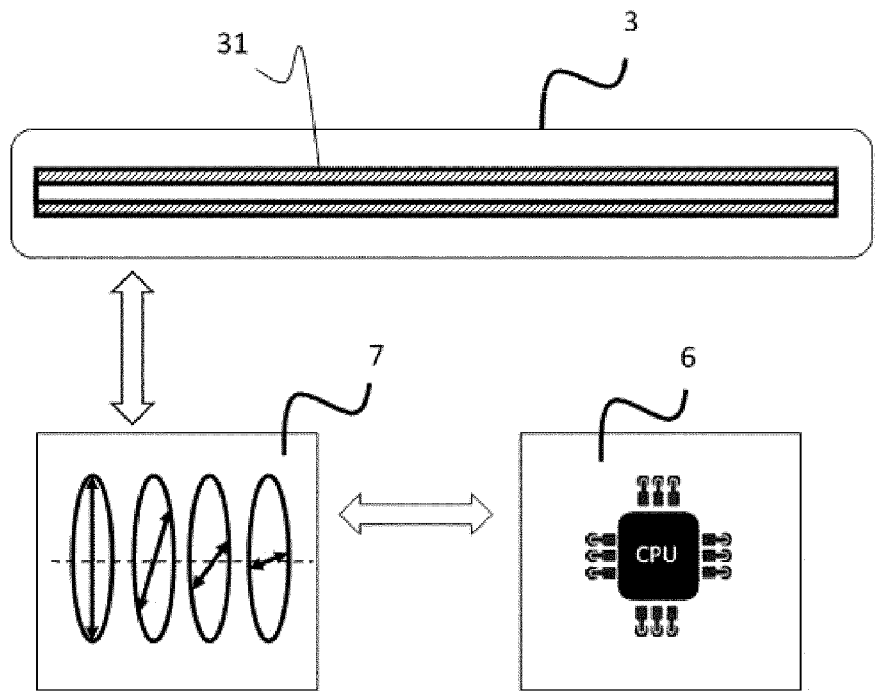
FIG. 3 is a schematic representation of an optical coupler, a polarization corrector and a control unit of the cutting apparatus.

Referring to FIG. 3, the cutting apparatus also comprises a polarization corrector 7.

This polarization corrector 7 allows modifying the polarization of the treatment laser beam 11 at the input of the optical coupler 3 so that the polarization of the treatment laser beam at the output of the optical coupler 3 is substantially equal to a desired reference polarization for the treatment laser beam before its introduction into the shaping system 2.

Indeed, as indicated above, the shaping system 2 allows modulating the phase of the treatment laser beam 11 derived from the laser source 1 to form intensity peaks in the focusing plane 81, each intensity peak producing a respective impact point in the focal plane corresponding to the cutting plane.

The phase modulation of the wavefront can be seen as a phenomenon of two-dimensional interferences. Each portion of the treatment laser beam 11 derived from the source 1 is delayed or advanced relative to the initial wavefront so that each of these portions is redirected so as to achieve constructive interference at N distinct points in the focal plane of a lens. This redistribution of energy into a plurality of impact points only takes place in a single plane (i.e. the focusing plane 81) and not all along the propagation path of the modulated treatment laser beam.

However, the shaping systems 2 are sensitive to the polarization of the incoming treatment laser beam. For example, in the case of a liquid crystal spatial light modulator, a "pure" phase modulation is possible if the polarization of the wavefront of the treatment laser beam entering the shaping system 2 is aligned with the extraordinary axis of the liquid crystals of the spatial light modulator.

Thus, to perform a "pure" phase modulation of the treatment laser beam 11 derived from the laser source 1, it is preferable that the polarization of the treatment laser beam entering the shaping system 2 corresponds to a desired reference polarization (for example in the case of a liquid crystal spatial light modulator, it is preferable that the polarization of the treatment laser beam entering the SLM is aligned with the optical axis of the liquid crystal).

However, the movement of the working head 204 to reach the working position induces changes in the position and orientation of the optical coupler (and particularly of the optical fiber of the coupler which can be twisted, etc.) which can modify the polarization of the treatment laser beam entering the shaping system 2.

This modification of the polarization of the treatment laser beam entering the shaping system 2 can degrade the quality of the modulated signal at the output of the shaping system 2.

The polarization corrector 7 allows correcting the polarization of the treatment laser beam entering the shaping system 2 so that the quality of the modulated treatment laser beam 21 exiting the shaping system 2 is optimal.

2.2. Elements Constituting the Polarization Corrector

The polarization corrector 7 is connected to the control unit 6 to allow the transmission of data measured by the polarization corrector 7 to the control unit 6 and to allow the transmission of monitoring signals emitted by the control unit 6 to the polarization corrector 7.

Figure 4:
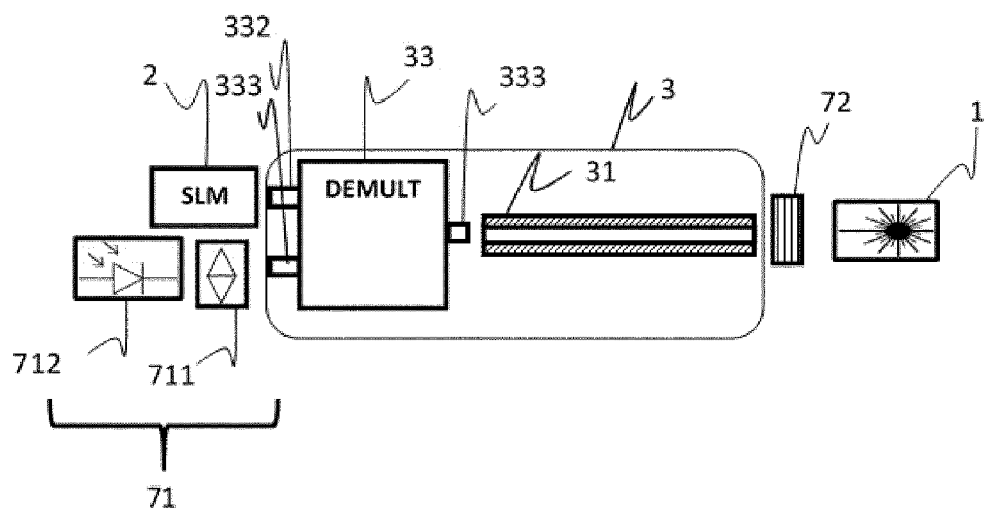
FIG. 4 is a detailed schematic representation of the optical coupler and the polarization corrector.

Referring to FIG. 4, the polarization corrector 7 comprises:
  means 71 for measuring the polarization variation of the treatment laser beam 11 between the input of the optical coupler 3 and the output of the optical coupler 3, and
  means 72 for modifying the polarization of the treatment laser beam 11 entering the optical coupler 3 so as to compensate for this measured variation in the polarization of the laser beam between the input and the output of the optical coupler.

2.2.1. Means for Measuring a Polarization Variation

Once the hinged arm 200 is in the working position, the measuring means 71 allow estimating the polarization modifications undergone by the treatment laser beam 11 when traveling through the optical coupler 3.

To measure the polarization modifications undergone by the treatment laser beam 11, the control unit 6 is programmed to drive the laser source 1 so that a measurement laser beam 12 is generated prior to the emission of the treatment laser beam 11, the intensity of the measurement laser beam 12 being much lower (in particular between 10 and 1,000 times lower) than the intensity of the treatment laser beam 11.

Thus, to measure the polarization modifications undergone by the treatment laser beam 11, the use of a measurement laser beam 12 (of low intensity) derived from the laser source 1 is preferred over the use of a polarized light beam derived from a secondary low-intensity polarized light source, such as a light-emitting diode associated with a linear polarizer.

The inventors have indeed discovered that identical polarization light beams derived from two different light sources do not undergo the same polarization modifications when traveling through the optical coupler 3.

In one embodiment, the measuring means 71 comprise a linear polarizer 711—such as a polarizer based on dielectric treatment, or a polarizer based on birefringent materials—and a polarization analyzer 712—such as a photodiode or a phototransistor—downstream of the linear polarizer 711.

The linear polarizer 711 allows selectively filtering the polarized light derived from the optical coupler 3. The polarization analyzer 712 allows measuring information representative of the polarization of the measurement laser beam 12 derived from the optical coupler 3.

The measuring means 71 are optically connected to the output of the optical coupler 3 via an optical demultiplexer 33, which can be integrated into the optical coupler 3 or into the linear polarizer 711.

More specifically, the optical coupler 3 comprises an optical demultiplexer 33 mounted at the end of the hollow-core photonic crystal fiber 31 closest to the shaping system 2.

The optical demultiplexer 33 includes:
  an input channel 333 optically connected to the photonic crystal fiber,
  a first output channel 331 optically connected to the shaping system 2 for allowing the transmission of the treatment laser beam 11 derived from the laser source 1 to the shaping system 2,
  a second output channel 332 optically connected to the measuring means 71 for allowing the transmission of the measurement laser beam 12 to the measuring means 71.

The optical demultiplexer 33 allows selecting the output channel 331, 332 on which the beam traveling through the input channel 333 (i.e. measurement or treatment laser beam) is transmitted in order to direct this beam either to the shaping system 2 or to the measuring means 71.

The operating principle of the means 71 for measuring the polarization variation of the laser beam between the input of the optical coupler 3 and the output of the optical coupler 3 is as follows. It is assumed here that the hinged arm 200 is in the working position that is to say the end 204 of the arm 200 (including the shaping system 2, the sweeping optical scanner 4 and the optical focusing system 5) extends above the ocular tissue to be treated.

Prior to the emission by the laser source 1, of the treatment laser beam 11 for the treatment of the tissue, the laser source 1 is activated by the control unit 6 to emit a low-intensity measurement laser beam 12. The measurement laser beam 12 enters the optical coupler 3 and travels through the photonic crystal fiber 31.

When traveling through the photonic crystal optical fiber 31, the polarization of the measurement laser beam 12 undergoes variations (for example rotation of the polarization plane due to twists of the photonic crystal optical fiber 31).

The measurement laser beam 12 then travels through the input channel 333 of the demultiplexer 33 and is switched to the second output channel 332 of the demultiplexer 33. The measuring means 71 sense the measurement laser beam 12. The polarization analyzer 712 measures information representative of the polarization of the measurement laser beam 12 received.

The information measured by the polarization analyzer 712 is transmitted to a computer of the measuring means 71 (which may or may not be integrated into the control unit 6). From this measured information, and knowing the polarization of the measurement laser beam 12 emitted by the laser source 1, the computer is able to calculate a polarization variation $\Delta_{polarization}$ between:

the polarization of the measurement laser beam 12 emitted by the laser source 1, and the polarization of the measurement laser beam 12 received by the polarization analyzer 712.

This calculated polarization variation is used by the computer to generate a compensation signal for correcting the polarization of the treatment laser beam 11 emitted by the laser source 1 so that the polarization of the treatment laser beam 11 at the output of the optical coupler 3 corresponds to a desired reference polarization for the treatment laser beam before its introduction into the shaping system 2.

This compensation signal is transmitted to the means 72 for modifying the polarization of the laser beam.

2.2.2. Means for Modifying the Polarization

The means 72 for modifying the polarization of the treatment laser beam allow correcting the polarization variation $\Delta_{polarization}$ measured by the measuring means 71.

The means 72 for modifying the polarization can be mounted downstream of the optical coupler 3. In this case, the means 72 for modifying the polarization are integrated into the end segment 204 (i.e. "working head") of the arm 200. This can induce bulk problems.

As a variant, the means 72 for modifying the polarization can be mounted between the laser source 1 and the optical coupler 3. This allows integrating the means 72 for modifying the polarization in the casing 210 of the therapy device (which limits the bulk problems). In this case, the means 72 for modifying the polarization allow generating a corrected polarization laser beam at the input of the optical coupler 3, so that the polarization of the laser beam at the output of the optical coupler 3 corresponds to a desired reference polarization.

More specifically, the polarization of the treatment laser beam 11 at the output of the laser source 1 corresponds to an optimal polarization, that is to say to the desired reference polarization for the treatment laser beam before its introduction into the shaping system 2.

Traveling through the photonic crystal optical fiber 31 modifies this polarization.

The means 72 for modifying the polarization allow compensating for the polarization modifications undergone by the treatment laser beam 11 when traveling through the photonic crystal optical fiber 31.

Thus, the polarization of the treatment laser beam 11 at the output of the optical coupler 3 corresponds to the optimal polarization of the treatment laser beam 11 at the output of the laser source 1.

The means 72 for modifying the polarization can comprise an electro-optical cell whose role is to rotate the polarization plane of the treatment laser beam 11 derived from the laser source 1 under the action of an electric control voltage. This cell can be of one of the types known to those skilled in the art to act on the light. For example, this cell may be a liquid crystal cell (such a crystal is particularly easy to control with a low expenditure of energy) or preferably a rotating waveplate—particularly a rotating half-wave plate—which has the advantage of being much less expensive than a liquid crystal cell.

The operating principle of the means 72 for modifying the polarization is as follows. It is assumed here that the means 72 for modifying the polarization are positioned between the laser source 1 and the optical coupler 3.

Once the compensation signal has been estimated by the computer, this compensation signal is sent to the means 72 for modifying the polarization in order to configure them.

When traveling through the means 72 for modifying the polarization, the polarization plane of the treatment laser beam 11 derived from the laser source 1 undergoes a rotation in the direction opposite to the measured polarization variation $\Delta_{polarization}$. A corrected polarization laser beam is obtained.

For example, if the measured polarization variation $\Delta_{polarization}$ corresponds to a rotation of the polarized light beam by an angle of 45° in the counterclockwise direction, the polarization plane of the treatment laser beam 11 derived from the laser source 1 is pivoted by an angle of 45° in the retrograde direction (i.e. angle of −45° in the counterclockwise direction).

Thus, at the output of the optical coupler 3, the polarization of the treatment laser beam 11 corresponds to the polarization of the treatment laser beam 11 at the output of the laser source 1.

The polarization corrector 7 allows modifying the polarization of the treatment laser beam 11 before its introduction into the shaping system 2. This solution allows maintaining all the power of the modulated laser beam 21 at the output of the shaping system 2 whatever the position and orientation of the end segment 204 (i.e. "working head") of the hinged arm 200.

3. CONCLUSIONS

The invention provides an efficient and accurate cutting tool. The reconfigurable modulation of the wavefront of the laser beam allows generating multiple simultaneous impact points each having a size and a position monitored in the focusing plane 81. These different impact points form a pattern in the focal plane 71 of the modulated laser beam.

The use of an optical coupler 3 including a hollow-core photonic crystal fiber 31 allows reducing the distance between the different impact points forming the pattern. Indeed, by limiting the phenomenon of spreading of the light spectrum, the optical coupler 3 including a hollow-core photonic crystal fiber 31 allows making the phase-modulated laser beam cleaner.

The presence of the polarization corrector 7 allows compensating for the polarization variations undergone by the treatment laser beam 11 when traveling through the optical coupler 3 so that the polarization of the treatment laser beam 11 at the input of the shaping system 2 corresponds to the desired polarization at the input of the shaping device.

The reader will understand that many modifications can be made to the invention described above without materially departing from the new teachings and advantages described here. Consequently, all such modifications are intended to be incorporated within the scope of the appended claims.

The invention claimed is:

1. A cutting apparatus for cutting human or animal tissue, said apparatus including:
a laser source configured for emitting a treatment laser beam in the form of pulses,
a shaping system positioned downstream of the laser source, configured for transforming the treatment laser beam into a single phase-modulated treatment laser beam, wherein the shaping system modulates the phase of the wavefront of the treatment laser beam according to a modulation set value calculated to distribute the energy of the single phase-modulated treatment laser beam into at least two impact points forming a pattern in a focusing plane,
an optical coupler between the laser source and the shaping system, wherein the optical coupler includes a photonic crystal fiber, and a polarization corrector mounted between the laser source and the shaping system, and configured for modifying the polarization of the treatment laser beam upstream of the optical coupler, wherein the polarization of the treatment laser beam downstream of the optical coupler corresponds to a desired reference polarization, and wherein the polarization corrector comprises:
  a sensor configured for measuring a polarization variation between an input end of the optical coupler and an output end of the optical coupler, and
  a polarization modifier configured for modifying the polarization of the treatment laser beam upstream of the optical coupler so as to compensate for the measured polarization variation.

2. The cutting apparatus according to claim 1, wherein the polarization corrector is mounted between the laser source and the shaping system, and wherein said polarization corrector modifies the polarization of the treatment laser beam upstream of the optical coupler so that the polarization of the treatment laser beam downstream of the optical coupler corresponds to the desired reference polarization.

3. The cutting apparatus according to claim 1, wherein the sensor is optically connected to the output end of the optical coupler, and wherein said sensor measures a polarization variation of a measurement laser beam generated by the laser source, the intensity of the measurement laser beam being lower than the intensity of the treatment laser beam.

4. The cutting apparatus according to claim 3, wherein the sensor comprises:
  a polarizer configured for selectively filtering a polarization plane of the measurement laser beam, and
  a polarization analyzer mounted downstream of the polarizer and configured for measuring information representative of the polarization of the measurement laser beam at the output of the optical coupler.

5. The cutting apparatus according to claim 4, wherein the sensor further comprises a computer configured for calculating, from the information measured by the polarization analyzer, a polarization variation $\Delta_{polarization}$ between:
  the polarization of the measurement laser beam emitted by the laser source, and
  the polarization of the measurement laser beam received by the polarization analyzer.

6. The cutting apparatus according to claim 1, wherein the polarization modifier is disposed between the laser source and the optical coupler, and wherein said polarization modifier pivots a polarization plane of the treatment laser beam upstream of the optical coupler by an angle opposite to the measured polarization variation.

7. The cutting apparatus according to claim 1, wherein the desired reference polarization is equal to the polarization of the treatment laser beam at the output of the laser source.

8. The cutting apparatus according to claim 1, which further comprises:
  a sweeping optical scanner, positioned downstream of the shaping system, configured for moving the pattern along a predefined movement path in the focusing plane,
  an optical focusing system, positioned downstream of the sweeping optical scanner, configured for moving the focusing plane of the modulated laser beam in a cutting plane for the human or animal tissue, and
  a control unit configured for driving the laser source, the shaping system, the optical coupler, the sweeping optical scanner and the optical focusing system.

9. A therapy device including a casing and a hinged arm mounted on the casing, the hinged arm including a plurality of arm segments connected by hinges, wherein the therapy device further comprises a cutting apparatus for cutting human or animal tissue, said apparatus including:
  a laser source configured for emitting a treatment laser beam in the form of pulses,
  a shaping system positioned downstream of the laser source, configured for transforming the treatment laser beam into a single phase-modulated treatment laser beam, wherein the shaping system modulates the phase of the wavefront of the treatment laser beam according to a modulation set value calculated to distribute the energy of the single phase-modulated treatment laser beam into at least two impact points forming a pattern in a focusing plane,
  an optical coupler between the laser source and the shaping system, wherein said optical coupler includes a photonic crystal fiber, and
  a polarization corrector mounted between the laser source and the shaping system and configured for modifying the polarization of the treatment laser beam upstream of the optical coupler wherein the polarization of the treatment laser beam downstream of the optical coupler corresponds to a desired reference polarization, and wherein the polarization corrector comprises:
    a sensor configured for measuring a polarization variation between an input end of the optical coupler and an output end of the optical coupler, and
    a polarization modifier configured for modifying the polarization of the treatment laser beam upstream of the optical coupler so as to compensate for the measured polarization variation,
  the shaping system, the sweeping optical scanner and the optical focusing system being mounted in an end segment of the hinged arm, the laser source and the control unit being integrated into the casing.

10. The therapy device according to claim 9, wherein the polarization modifier is integrated into the casing.

11. The therapy device according to claim 9, wherein the polarization corrector is mounted between the laser source and the shaping system, and wherein said polarization corrector modifies the polarization of the treatment laser beam upstream of the optical coupler so that the polarization of the treatment laser beam downstream of the optical coupler corresponds to the desired reference polarization.

12. The therapy device according to claim 9, wherein the sensor is optically connected to the output end of the optical coupler, and wherein said sensor measures a polarization variation of a measurement laser beam generated by the laser source, the intensity of the measurement laser beam being lower than the intensity of the treatment laser beam.

13. The therapy device according to claim 12, wherein the sensor comprises:
  a polarizer configured for selectively filtering a polarization plane of the measurement laser beam, and
  a polarization analyzer mounted downstream of the polarizer and configured for measuring information representative of the polarization of the measurement laser beam at the output of the optical coupler.

14. The therapy device according to claim 13, wherein the sensor further comprises a computer configured for calculating, from the information measured by the polarization analyzer, a polarization variation $\Delta_{polarization}$ between:
  the polarization of the measurement laser beam emitted by the laser source, and
  the polarization of the measurement laser beam received by the polarization analyzer.

15. The therapy device according to claim 9, wherein the polarization modifier is disposed between the laser source and the optical coupler, and wherein said polarization modifier pivots a polarization plane of the treatment laser beam upstream of the optical coupler by an angle opposite to the measured polarization variation.

16. The therapy device according to claim 9, wherein the desired reference polarization is equal to the polarization of the treatment laser beam at the output of the laser source.

17. The therapy device according to claim 9, which further comprises:
- a sweeping optical scanner, positioned downstream of the shaping system, configured for moving the pattern along a predefined movement path in the focusing plane,
- an optical focusing system, positioned downstream of the sweeping optical scanner, configured for moving the focusing plane of the modulated laser beam in a cutting plane for the human or animal tissue, and
- a control unit configured for driving the laser source, the shaping system, the optical coupler, the sweeping optical scanner and the optical focusing system.

* * * * *